(12) United States Patent
Gregoire et al.

(10) Patent No.: US 8,632,790 B2
(45) Date of Patent: Jan. 21, 2014

(54) SKIN CARE PAD

(75) Inventors: Philippe Gregoire, Les Andelys (FR); Bernard Louis Dit Picard, Amfreville la Campagne (FR)

(73) Assignee: SCA Tissue France, Bois-Colombes (FR)

( * ) Notice: Subject to any disclaimer, the term of this patent is extended or adjusted under 35 U.S.C. 154(b) by 2045 days.

(21) Appl. No.: 10/567,804

(22) PCT Filed: Aug. 9, 2004

(86) PCT No.: PCT/FR2004/002113
§ 371 (c)(1),
(2), (4) Date: Feb. 9, 2006

(87) PCT Pub. No.: WO2005/016099
PCT Pub. Date: Feb. 24, 2005

(65) Prior Publication Data
US 2007/0082032 A1    Apr. 12, 2007

(30) Foreign Application Priority Data
Aug. 12, 2003   (FR) ...................................... 03 09868

(51) Int. Cl.
*A61K 8/00*       (2006.01)
*C11D 3/12*       (2006.01)

(52) U.S. Cl.
USPC ............ 424/401; 510/130; 510/139; 510/334

(58) Field of Classification Search
None
See application file for complete search history.

(56) References Cited

U.S. PATENT DOCUMENTS

| 6,902,338 B2 * | 6/2005 | Puvvada et al. ............... 401/201 |
| 7,037,866 B2 * | 5/2006 | Michaud ....................... 442/408 |
| 2002/0107528 A1 | 8/2002 | Vayrette |
| 2003/0031703 A1 * | 2/2003 | McMeekin et al. ........... 424/443 |

FOREIGN PATENT DOCUMENTS

| EP | 1283019 A1 | 2/2003 |
| EP | 1350456 A1 | 10/2003 |
| FR | 2819390 | 7/2002 |
| WO | WO 01/66345 A1 | 9/2001 |
| WO | WO 02/43536 A2 | 6/2002 |

* cited by examiner

*Primary Examiner* — Michael G Hartley
*Assistant Examiner* — Nabila Ebrahim
(74) *Attorney, Agent, or Firm* — Drinker Biddle & Reath LLP

(57) ABSTRACT

The invention relates to a skin care pad comprising exfoliating elements (4) which are distributed between at least one first fibrous layer (2) and a second fibrous layer (6), said second layer having a lower basis weight than the first fibrous layer. In this way, the inventive pad can be used daily, in order to exfoliate and massage the skin and to remove make-up.

20 Claims, 1 Drawing Sheet

SKIN CARE PAD

Figure 1:
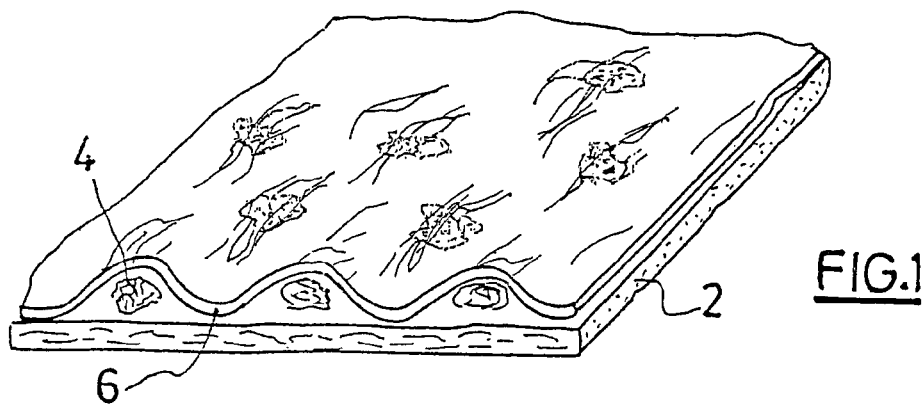

This invention relates to a pad made up of fibers of cotton or other cellulose or synthetic materials and is intended for care of the skin, a pad in particular possessing the property of being exfoliating.

The treatment of exfoliation is known in particular in the area of skin care in the field of cosmetic products. It involves action permitting elimination of encrusted impurities which accumulate on the surface of the epidermis and of dead cells by a mechanical exfoliating action. Exfoliation permits improvement in the texture of the skin, purification of the epidermis, and clearing up of the complexion. Conventionally, use is made of natural fibers. Known examples are luffa or fibrous gourd bread, the flesh glove, and the hemp or even sisal glove. However, these fibers cause a rough exfoliation that may be carried out only occasionally, once a week or even once a month. Exfoliating preparations are also known which have natural, organic, or plant elements such as strawberry achenes, cracked apricot kernels, organic bamboo silica, gourd cellulose, or elements of the mineral type, such as balls of silica, or artificial and/or synthetic elements. This includes all polymers, such as polyethylene, nylon, polypropylene, EVA (ethylene vinyl acetate), and so forth. The current market trend is based on these last-named elements in the form of microbeads, which permit gentler exfoliation depending on the nature of the material. Breakable spheres releasing active principles may also be used.

EP 1 283 019 A1 discloses a pad for skin care consisting of exfoliating elements deposited as a layer on one of its surfaces. Additionally, by way of technological background information, mention is made of the following applications. FR 2 819 390 also discloses a glove formed with a nonwoven product one of whose sides is more corrugated than the other. The object of WO 01/66345 A1 is to achieve a non woven product consisting of three layers of the thermally bonded airlaid type that are then calendered and embossed in order to form moist wipes. WO 02/43536 discloses a nonwoven wipe each side of which has a different texture, one relatively soft and the other relatively abrasive in order to perform two different functions during household cleaning operations.

This invention relates to an article for skin care which is intended for daily use.

Another object of the invention is the creation of an article that may be used at the same time in order to exfoliate and massage the skin and to remove make-up.

It is claimed for the invention that this object is attained by means of a pad for skin care comprising exfoliating elements distributed between at least one first fibrous layer and a second fibrous layer having a lower basis weight than the first fibrous layer.

The solution claimed for the invention thus makes it possible to obtain an exfoliating effect as a result of application of the surface comprising exfoliating elements under a fibrous layer of low basis weight on the skin with movement dynamics.

A massaging effect is obtained as a result of the geometry of the surface and its movement on the skin.

Because of the layer of fibers of lower basis weight, the mechanical effect is attenuated, this making it possible to obtain a very gentle exfoliation and thus permitting daily use.

Use of absorbent fibers in at least one of the layers makes intensified makeup removal action possible because of the mechanical action of the massaging elements supplemented by absorption of the fibers which trap the makeup. Since the makeup removal is more efficient, it is faster. The skin is less irritated; it remains more supple.

The massaging elements preferably form a layer and the basis weight of the layer of massaging elements ranges from 2 to 50 $g/m^2$. The massaging elements selected are natural organic products such as strawberry achenes, cracked apricot kernels, organic bamboo silica, gourd cellulose, or, more innovatively, flax chaff, natural minerals such as silica beads, or artificial ones such spheres of cellulose, and methylcellulose or synthetic ones such as polymers of polyethylene, nylon, polypropylene, or EVA.

The fibrous layers advantageously consist of fibers selected from among cellulose, artificial fibers and synthetic fibers, either individually or in a mixture.

The first layer consists in particular of fibers selected from among cotton, viscose, polyester, and polypropylene fibers, either individually or in a mixture, and its basis weight ranges from 20 to 350 $g/m^2$. The first layer advantageously is a sheet of fibers of the pneumatic sheeting type, for example formed on a machine of the Rando Webber type. It may also consist of a sheet and of a carded web or even several carded webs.

Similarly, the second layer in particular consists of fibers selected from among fibers of cotton, flax, viscose ramie, polyester, polypropylene, individually or in a mixture, and its basis weight ranges from 5 to 50 $g/m^2$. It is lower than that of the first layer.

The second layer advantageously consists of one or more fibrous webs.

In one particular embodiment, the pad comprises a second layer of exfoliating elements introduced between the first layer and a third fibrous layer of a basis weight lower than that of the first layer.

The fibrous layers advantageously are connected and in particular are interconnected, for example, by hydroentanglement or mechanical bonding or, when the layers comprise at least one part of a thermofusible substance, the fibers are at least in part thermally bonded.

The invention also relates to a process of manufacturing such a pad. It comprises the following stages: formation of a first layer of fibers, depositing of a layer of exfoliating elements on the first layer, and depositing of a second layer of fibers on the layer of exfoliating elements.

Figure 2:
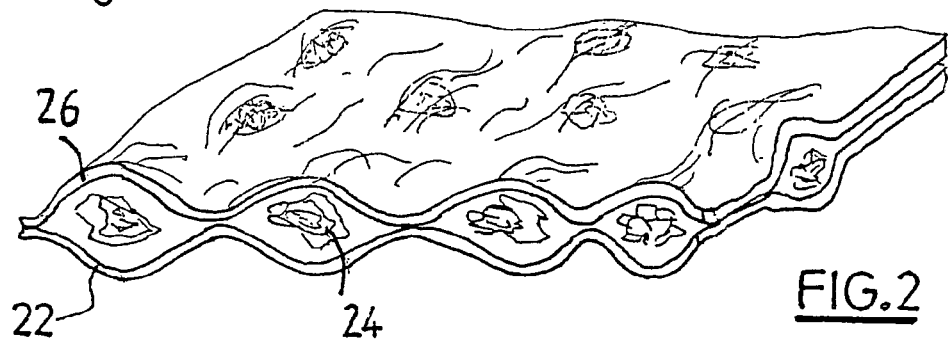
Figure 3:
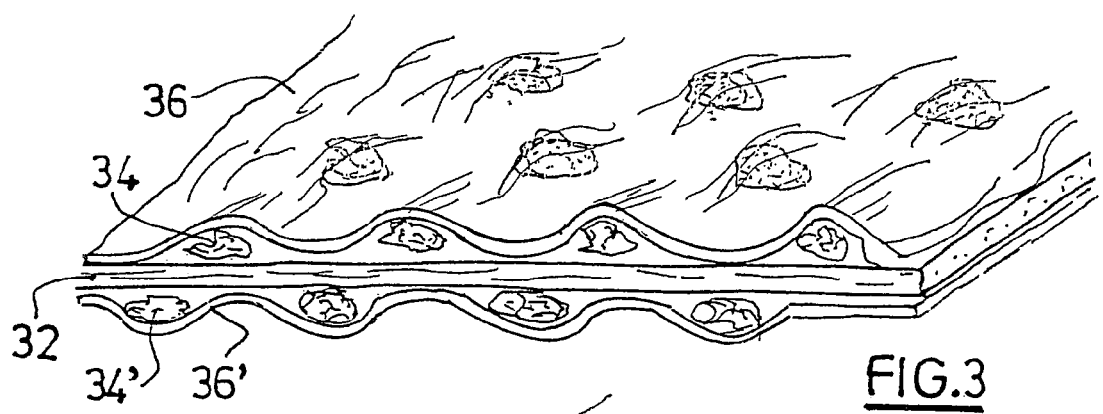
Figure 4:
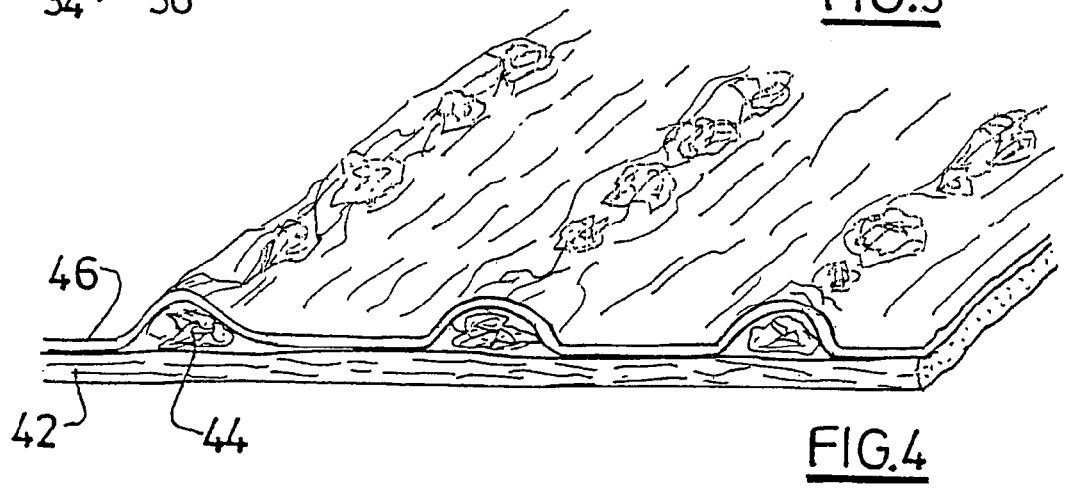

The invention will be better understood by reading the following description of the various embodiments with respect to the accompanying drawings, in which FIG. 1 presents an illustration of a structure of the pad claimed for the invention, as seen in a perspective view of a cross-section, FIGS. 2 to 4 illustrate alternative structures of the pad.

As is seen in FIG. 1, the product claimed for the invention includes a first layer of fibers 2 serving to support a layer of exfoliating elements 4 distributed evenly or in a specific pattern on its surface. The exfoliating elements are held in place by a layer of fibers 6 which are fine enough so that they do not mask the effect of the layer of exfoliating elements on the skin.

Preferably for the first layer, use is made of a layer of fibers formed by a machine of the Rando Webber type which arranges the fibers with a specific orientation at an angle in relation to the direction of formation of the sheet of fibers. Consequently, the layer is relatively thick. Use is advantageously made of fibers of water absorbent cotton. However, as has been pointed out earlier, other categories of fibers are possible. The basis weight of layer 2 ranges from 20 to 350 $g/m^2$.

The exfoliating layer is made up of elements that are known in the field of cosmetics to possess exfoliating properties tolerated by the skin. These elements are such as that referred to earlier of an organic, mineral, artificial, or synthetic nature. The elements are in the form of fibers, granules or microspheres; the basis weight of the layer of exfoliating elements 4 ranges from 2 to 50 g/m².

The upper layer 6 is made up of a second fibrous layer intended to form a sandwich structure with the first layer 2, the elements of the exfoliating layer 4 being inserted between the two layers. This layer advantageously consists of one or more fibrous webs. The advantage of the fibrous web is to offer a certain resistance to any bonding of fibers in another manner while remaining fine enough not to mask the corrugation of the underlying elements. The basis weight of the layer ranges from 5 to 50 g/m². It is preferably always lower than that of the first layer, which functions rather as a support.

In use, the skin is rubbed by applying the side of the pad with the second layer 6 to obtain an exfoliating effect and simultaneous massaging effect. The second surface in the direction of the first layer of fibers 2 is used for wiping, for example. It is necessarily softer, since the exfoliating particles are not felt through it or are felt to a lesser extent.

The product as a whole may be left in the form of unbonded layers; however, because the product as a whole, especially when subjected to an exfoliating action, would lack cohesion, by preference the layers are interconnected. They may, for example, be bonded hydraulically or mechanically or by another means yielding an equivalent result. The pad may also contain a thermofusible substance and fibers may be at least in part thermally bonded.

The invention is not, however, limited to this structure. FIG. 2 illustrates an embodiment in which the first layer 22 acting as support is also a carded web or a plurality of carded webs. Also to be seen in the pad shown in FIG. 2 is a layer 24 of exfoliating elements as in the embodiment shown in FIG. 1 and an upper fibrous layer 26.

In the embodiment shown in FIG. 3, a pad with two exfoliating surfaces has been created, cohesion of the product as a whole being ensured by a center layer, which by preference is thicker. The pad thus includes a center layer 32 which may be a carded web but preferably is a sheet as in the case of the first layer of the embodiment shown in FIG. 1. A layer 36 and 36' is present on each side of the first layer 32. In this instance as well these layers can be carded webs. The layers of exfoliating elements, 34 and 34' respectively, are sandwiched between layers 32 and 36 on one side and layers 32 and 36' on the other.

FIG. 4 illustrates an embodiment in which the exfoliating elements 44 are distributed over the surface of the first layer 42 spaced at regular intervals. For example, the elements may be arranged in lines or strips or in any other continuous or broken pattern. A contour clearly marked by alternating protuberances and flat surfaces is thus obtained. As is the other embodiments, they are kept by the upper layer 46 which is lighter than the layer 42.

In another structure, not shown, one or more carded webs is/are arranged on the free surface of the first layer so as to make contact with the surface opposite the exfoliating surface more gentle.

The invention is not limited to the embodiments presented in the foregoing; it incorporates all the variant embodiments knowable to any person skilled in the art.

The invention claimed is:

1. A pad for skin care comprising a fibrous sheet comprising:
    a first fibrous layer;
    a second fibrous layer having a lower basis weight than the basis weight of the first fibrous layer; and
    a layer of exfoliating elements between the first fibrous layer and the second fibrous layer,
    wherein the second layer does not mask the effect of the underlying exfoliating elements thereby forming a plurality of protuberances at an outer surface of the second layer for effecting exfoliation, and
    wherein the second layer has sufficient basis weight to attenuate mechanical effects of the underlying exfoliating elements compared to if the exfoliating elements were applied directly to a user's skin.

2. The pad according to claim 1, wherein the layer of exfoliating elements is a continuous layer.

3. The pad according to claim 1, wherein the layer of exfoliating elements is evenly distributed.

4. The pad according to claim 1, wherein the layer of exfoliating elements has a broken pattern.

5. The pad according to claim 1, wherein the first and second fibrous layers consist of fibers selected from among cellulose fibers, artificial fibers, or synthetic fibers, individually or in a mixture.

6. The pad according to claim 5, wherein the first fibrous layer consists of fibers selected from among the fibers of cotton, viscose, polyester, or polypropylene, individually or in a mixture.

7. The pad according to claim 1, wherein the basis weight of the first fibrous layer ranges from 20 to 350 g/m².

8. The pad according to claim 1, wherein the first fibrous layer is a sheet of fibers formed on a machine of the Rando Webber type.

9. The pad according to claim 5, wherein the second fibrous layer consists of fibers selected from among the fibers of cotton, flax, ramie, viscose, polyester, or polypropylene, individually or in a mixture.

10. The pad according to claim 1, wherein the basis weight of the second fibrous layer ranges from 5 to 50 g/m2.

11. The pad according to claim 1, wherein the second fibrous layer consists of one or more carded webs.

12. The pad according to claim 1, wherein the basis weight of the layer of exfoliating elements ranges from 2 to 50 g/m².

13. The pad according to claim 1, wherein the exfoliating elements are selected from among
    natural organic products, such as strawberry achenes, apricot kernels, organic bamboo silica, or gourd silica,
    mineral products, such as beads of silica,
    artificial products, such as spheres of cellulose and methylcellulose,
    or synthetic products, such as the polymers polyethylene, nylon, polypropylene, or EVA.

14. The pad according to claim 1, further comprising a second layer of exfoliating elements between the first fibrous layer and a third fibrous layer.

15. The pad according to claim 1, wherein the fibrous layers are bonded.

16. The pad according to claim 1, wherein the layers are bonded to each other.

17. The pad according to claim 16, wherein the fibers of the fibrous layers are bonded to each other by hydraulic bonding or mechanical bonding.

18. The pad according to claim 15, wherein such pad comprises at least thermofusible material and its fibers are at least in part thermally bonded.

19. A process of manufacturing a pad according to any one of claims 1-18, comprising the following stages: formation of a first layer of fibers, depositing of a layer of exfoliating elements on the layer, and depositing of a second layer of fibers on the layer of exfoliating elements.

20. The pad according to claim 1, wherein the exfoliating elements in the layer of exfoliating elements are spaced apart between the first fibrous layer and the second fibrous layer, and are held in place by the second fibrous layer.

\* \* \* \* \*